United States Patent
Georgieff et al.

[11] Patent Number: 5,520,169
[45] Date of Patent: May 28, 1996

[54] ANESTHESIA ARRANGEMENT FOR RECOVERING GASEOUS ANESTHETIC AGENTS

[75] Inventors: Michael Georgieff, Blaustein; Thomas Marx, Ulm; Stefan Bäder, Senden, all of Germany

[73] Assignee: Drägerwerk Aktiengesellschaft, Lübeck, Germany

[21] Appl. No.: 406,414

[22] Filed: Mar. 20, 1995

[30] Foreign Application Priority Data

Apr. 2, 1994 [DE] Germany .......................... 44 11 533.4

[51] Int. Cl.⁶ ................................................ A61M 16/00
[52] U.S. Cl. .................... 128/204.16; 128/203.29; 128/204.22; 128/205.12; 128/205.27; 128/910
[58] Field of Search ................... 128/201.21, 203.12, 128/203.29, 204.15, 204.16, 204.18, 204.21, 204.22, 205.12, 205.25, 205.27, 910; 210/774, 808; 55/267, 466; 62/11, 22, 36

[56] References Cited

U.S. PATENT DOCUMENTS

| | | | |
|---|---|---|---|
| 3,592,191 | 7/1971 | Jackson | 128/204.16 X |
| 3,707,066 | 12/1972 | Carne et al. | 62/11 X |
| 3,721,097 | 3/1973 | Briley et al. | 62/11 |
| 4,903,693 | 2/1990 | Yasue | 128/203.12 |
| 4,905,685 | 3/1990 | Olsson et al. | 128/203.12 |
| 5,044,361 | 9/1991 | Werner et al. | 128/204.16 |

FOREIGN PATENT DOCUMENTS

| | | |
|---|---|---|
| 0287068 | 10/1988 | European Pat. Off. |
| 0576314 | 12/1993 | European Pat. Off. ............... 62/22 |
| 3000191 | 7/1980 | Germany. |

*Primary Examiner*—Edgar S. Burr
*Assistant Examiner*—Eric P. Raciti
*Attorney, Agent, or Firm*—Walter Ottesen

[57] ABSTRACT

The invention is directed to an anesthesia arrangement having a pump device for returning preselected gaseous components from an expiration line 2 of the anesthesia apparatus 1 into a first pressure vessel 17. The anesthesia arrangement is so improved that the rinsing losses are minimized and the anesthetic agent is available at constant concentration. The arrangement includes a second pressure vessel 19 connected downstream of the first pressure vessel 17 and a compressor 18 for pumping the gaseous components from the first pressure vessel into the second pressure vessel. The compressor 18 and a cooling unit 20 adjust the operating parameters of pressure and temperature so that at least the anesthetic agent is present in the liquid phase in the second pressure vessel.

7 Claims, 1 Drawing Sheet

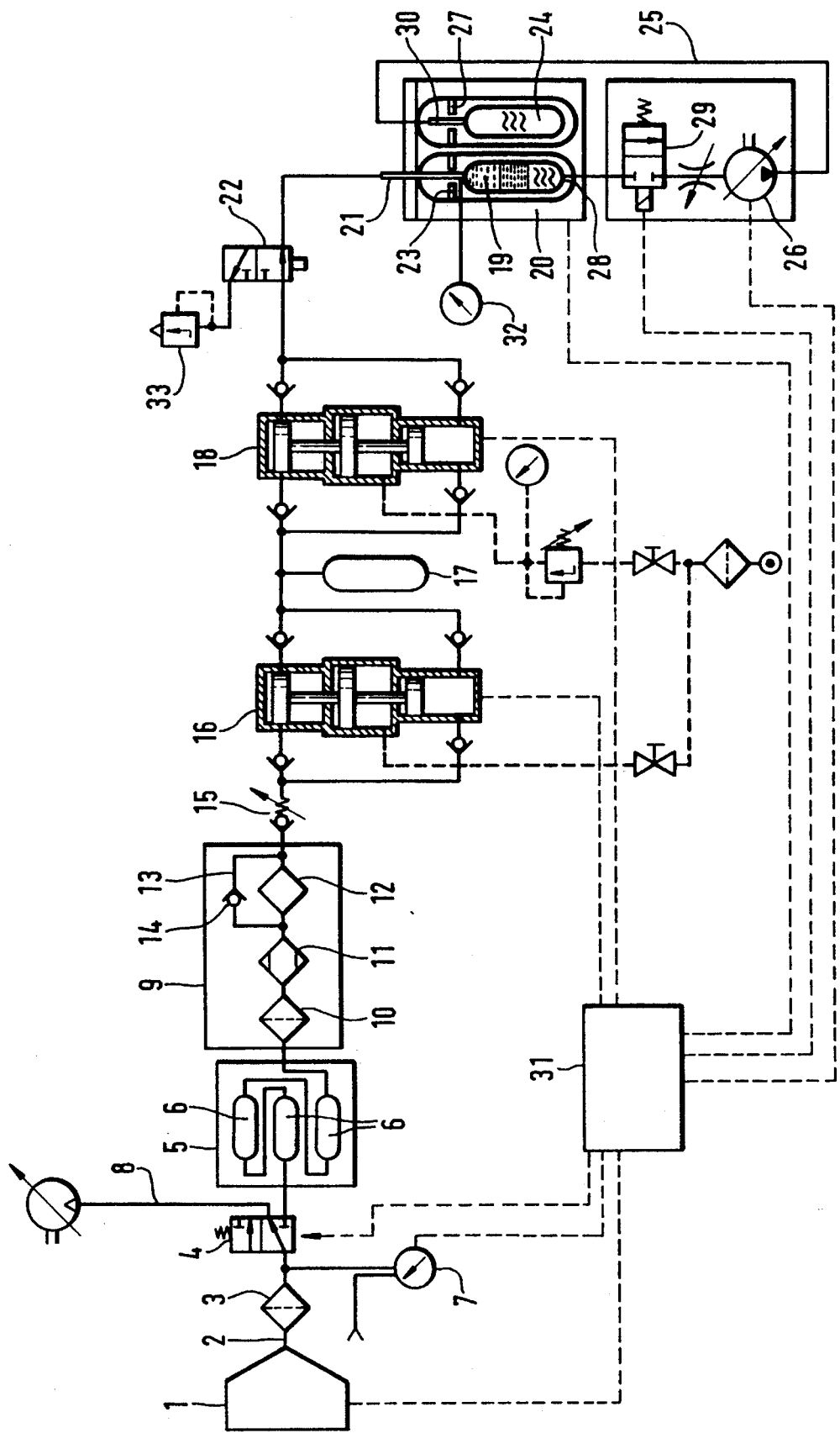

ANESTHESIA ARRANGEMENT FOR RECOVERING GASEOUS ANESTHETIC AGENTS

FIELD OF THE INVENTION

The invention relates to an anesthesia arrangement for ventilating a patient with a respiratory gas containing an anesthetic agent and having a pump device for returning predetermined gas components from an expiration line of the anesthesia apparatus via a cleaning unit into a first pressure vessel.

BACKGROUND OF THE INVENTION

For more than a century, gaseous anesthesia drugs have been utilized in anesthesia. An anesthesia gas which is liquid at room temperature and atmospheric pressure and is vaporized in an anesthesia vaporizer, is identified as being a volatile anesthetic agent. Gaseous anesthetic agents are also available.

Chloroform and ether were used as early volatile anesthetic agents and have been replaced with various further developments in the course of the past years for medical and safety reasons. Halothane (C—F$_3$—C—H—Cl—Br) was developed in the 1950's and is a present day anesthetic agent in general use. Other anesthetic agents in use today are Enflurane (C—F$_2$—H—O—C—F$_2$—C—F—Cl—H) and Isoflurane (C—F$_2$—H—O—C—H—Cl—C—F$_3$) which have been developed in the 1980's.

Nitrous oxide (N$_2$O) is used for all anesthesia as a gaseous anesthetic agent and carrier gas. Nitrous oxide increases the effect of the anesthetic substances and thereby reduces their use. The inspiratory nitrous oxide concentration amounts usually to 70%. The concentrations of volatile anesthetic agents required for the anesthesia amount to between 1% and 2% in the inspiratory air of the patient. For a general anesthesia, the patient, as a rule, is ventilated with an anesthesia gas mixture of 70% N$_2$O, 30% oxygen and the particular volatile anesthetic agent. Halothane is metabolized by humans at 20%, enflurane at 2% and isoflurane at 0.2%. Nitrous oxide is exhaled unchanged.

In modern anesthesia ventilating apparatus, it is necessary for technical reasons to meter a far greater quantity of gas to the patient than is justified by the actual consumption. The excess gas is conducted into the anesthesia gas removal line. A possibility of reducing the consumption of anesthesia gases is the low-flow anesthesia. The gas flow in the low-flow anesthesia amounts to ⅓ to ⅙ of that which is conventional in modern gas anesthesia. In order to be able to control the metering of gas with adequate precision, the low-flow anesthesia requires a ventilating apparatus which has a more complicated configuration than those apparatus which have been utilized up to now. For example, they must be tighter and be made with greater precision in order to meter the required gas concentration for anesthesia with adequate precision. Low-flow anesthesias are basically possible with the technical possibilities provided today and with the introduction of a new generation of anesthesia ventilating apparatus; however, this cannot be utilized in all surgery.

It is known since the 1940's that the rare gas xenon is suitable as an inhalation anesthetic agent. Xenon affords many advantages medically. Advantages have been found when compared to nitrous oxide in investigations which have been carried out utilizing xenon as an inhalation anesthetic agent. These advantages include: a sleep which has been found to be very pleasant by the patient, higher circulatory stability, lack of release of stress hormones and advantages for the local circulation of individual organs. Xenon acts anesthetically stronger than nitrous oxide from which an additional anesthetic-agent saving effect results. Also, xenon is better suited than nitrous oxide and isoflurane for the low-flow anesthesia because of its lower blood/gas solubility and therefore builds up more rapidly and reduces more rapidly in the body. Also, xenon as a rare gas is with the greatest probability of no problem when considered in the context of environmental and workplace exposure aspects. For the above reasons, xenon is regarded as a virtually ideal anesthetic gas. The only disadvantage of xenon has been its high cost. For this reason, it has been pointed out in almost all investigations that xenon is only suitable for scientific purposes and cannot be considered for clinical use.

The use of xenon as an inhalation anesthetic agent would be a significant advance in the area of medical applications and in the exposure to the environment and workplace. The high cost of xenon, however, makes an adequate recovery method absolutely necessary.

Published European patent application 0,287,068 discloses an anesthesia apparatus for ventilating a patient with xenon as a constituent of the respiratory gas. The respiratory gas here comprises a gas mixture of oxygen and xenon and is supplied to the patient via an inspiratory line and is conducted back to the anesthesia apparatus via an expiratory line. A cleansing unit is disposed in the expiration line and includes a filter for the adsorption of carbon dioxide and water. The cleansing unit also has an active charcoal filter. The expired respiratory gas which is so cleaned is pumped into two pressure vessels by a compressor operating as a pumping device. The pressure vessels, in addition to oxygen, contain either a concentration of xenon less than 80% or greater than 80%. The expired respiratory gas is analyzed with respect to its xenon content and, depending upon the measured xenon concentration, is supplied to one or the other pressure vessel. The pressure vessels are connected to the gas mixer of the anesthesia apparatus and function as a reservoir for the inspirated respiratory gas supplied to the patient.

Although the known anesthesia apparatus permits a substantial recovery of xenon from the expiratory respiratory gas one is, however, dependent upon the instantaneous gas-type composition present in the pressure vessels when adjusting the inspiratory xenon concentration. This composition can change continuously because of the continuous return of the expiratory respiratory gas. A continuous control of the xenon concentration, which is present in the pressure vessels, is necessary and this makes the manipulation of the apparatus overall difficult. Furthermore, xenon is lost because of the purging operations within the expiratory line. This xenon cannot be returned to the two pressure vessels and must be separately processed.

Published German patent application 3,000,191 discloses a method for recovering xenon from exhaled respiratory gas. This method is based on the adsorption of xenon in heated active charcoal beds with a subsequent desorption utilizing a purging gas. It is disadvantageous in this method that only a portion of the inhaled xenon volume can be recovered and that an application in the clinical routine operation is not possible because of the high complexity of the apparatus.

SUMMARY OF THE INVENTION

It is an object of the invention to improve an anesthesia arrangement for recovering the anesthetic agent metered to the patient in such a manner that rinsing losses are minimized and that the recovered anesthetic agent is available with a constant concentration.

The anesthesia arrangement of the invention is for ventilating a patient with a respiratory gas containing an anesthetic agent and includes: an anesthesia apparatus having an expiration line for passing the respiratory gas from the patient; a purification unit connected to the expiration line for removing contaminants and predetermined vaporous or gaseous components from the respiratory gas so as to leave a purified respiratory gas containing the anesthetic agent and any remaining vaporous or gaseous component or components; a first pressure vessel; pump means for pumping the respiratory gas through the purification unit and pumping the purified respiratory gas into the first pressure vessel; a second pressure vessel connected to the first pressure vessel downstream thereof; compressor means for moving the purified respiratory gas from the first pressure vessel and into the second pressure vessel; cooling means for cooling the second pressure vessel; and, control means for controlling the compressor means and the cooling means to operating parameters within the second pressure vessel which cause the anesthetic agent to assume a liquid phase in the second pressure vessel.

The advantage afforded by the invention is seen essentially in that, on the one hand, rinsing losses of the anesthetic agent caused during operation no longer occur because the total gas, which is in the first pressure vessel, is pumped into the second pressure vessel and, on the other hand, the separation of the anesthetic agent from the remaining gas constituents takes place by condensing out the anesthetic agent in the second pressure vessel whereby this anesthetic agent is again available in virtually pure form with a constant concentration component and can again be used for a new inhalation anesthesia. If further constituents of the gas mixture are liquified in the second pressure vessel, a stratification or layering of the liquified gases occurs in correspondence to the specific weights of the individual constituents. If the anesthetic agent xenon is used, then xenon is heavier than the remaining constituents of the expirated gas mixture and collects on the bottom of the second pressure vessel.

In an advantageous manner, a pressure P of approximately 60 bar and a temperature T of approximately 10° C. is set. The temperature T is less than the critical temperature of the anesthetic agent to be liquified. In this case, the temperature T is less than the critical temperature of xenon.

The temperature T in combination with the pressure P in the second pressure vessel are adjusted so that they are less than the critical temperature of the anesthetic agent but yet are greater than the critical temperature of that gaseous component which would be the next to change into the liquid phase when reaching this temperature. In this way, only the anesthetic agent to be recovered is present in the liquid phase in the second pressure vessel; whereas, the remaining constituents are present in the gaseous state.

The second pressure vessel includes a pump line for the liquid anesthetic agent and this pump line opens into a third pressure vessel. Liquified anesthetic agent can be transferred from the second pressure vessel into the third pressure vessel via the pump line.

A pump device is advantageously provided in the pump line to transport liquid anesthetic agent from the second pressure vessel into the third pressure vessel.

A discharge device is advantageously provided on the second pressure vessel for the gaseous constituents which are present above the liquified gaseous components. The discharge device is configured in such a manner that it permits a flow of gas from the compression device into the second pressure vessel in a rest mode and interrupts the gas flow in an operating mode and permits gaseous constituents to flow out from the second pressure vessel via a discharge throttle. The discharge of gaseous constituents from the second pressure vessel is controlled in dependence upon the pressure present in the second pressure vessel. For example, if the pressure in the second pressure vessel has reached a value $P_{max}$, then the discharge device switches over into the operating mode and the pressure P is reduced to a value $P_{min}$. Thereafter, the discharge device is switched over into its rest position and the pressure P in the second pressure vessel is again increased to $P_{max}$. With this alternating "compression" and "discharge", the portion of the liquid anesthetic agent slowly increases in the second pressure vessel.

In an advantageous manner, the purification unit connected to the expiration line of the anesthesia apparatus comprises at least one sorption filter and a temperature device for adjusting the temperature of the gaseous constituents to a specific value. The sorption filter has a particle filter and an active-charcoal filter for the adsorption of specific gaseous components to be removed from the respiratory gas such as acetone and ethanol which are formed by the metabolism of the patient. Specific gaseous constituents from the respiratory gas, such as moisture, can be frozen out with the temperature device. The purification unit can also be provided with molecular sieves with which, for example, nitrogen, nitrous oxide and carbon dioxide can be adsorbed.

BRIEF DESCRIPTION OF THE DRAWING

The invention will now be described with reference to the drawing wherein the single FIGURE is a schematic showing an anesthesia arrangement for ventilating a patent with a respiratory gas containing an anesthetic agent.

DESCRIPTION OF THE PREFERRED EMBODIMENTS OF THE INVENTION

Referring to the drawing, an anesthesia apparatus 1 ventilates a patient (not shown) with a respiratory gas containing an anesthetic agent. In this case, xenon is used as an anesthetic agent. The respiratory gas containing xenon flows out of an expiration line 2 of the anesthesia apparatus. The respiratory gas then flows into a reservoir 5 via a particle filter 3, and a safety valve 4. The reservoir 5 comprises three elastic vessels 6 connected in series to smooth the volume flow which flows discontinuously from the expiration line 2 and to compensate for pressure fluctuations. The particle filter 3 functions as a prefilter in order to keep contaminants away from a downstream difference pressure sensor 7 and the safety valve 4. The difference pressure sensor 7 measures the pressure rearward of the particle filter 3 with respect to atmospheric pressure. If the pressure increases above a preselected limit value, then the respiratory gas flowing from the expiration line 2 is directed into an anesthesia gas transport line 8 by the safety valve 4.

In the switching position of the safety valve 4 shown, the expiration line 2 is connected to the anesthesia gas transport line 8. A purification unit 9 is connected downstream of the reservoir 5 and this unit is, in turn, connected in series with the following: a sorption filter 10 having a prefilter for suspended particles greater than 1 micrometer, a fine filter for suspended particles greater than 0.1 micrometer and an active charcoal filter, a temperature device 11 for directly freezing out vaporous constituents and a molecular sieve 12 for adsorbing specific gases such as nitrogen, carbon dioxide and nitrous oxide. A return line 13 having a check valve 14 is provided on the molecular sieve 12 for recirculating the expiration gas. A throttle check valve 15 is mounted rearward of the molecular sieve 12 in order to prevent reactions on the purification unit 9.

The expiration gas in the reservoir 5 is drawn by suction via a pump device 16 and compressed in a first pressure vessel 17 to a pressure of approximately 10 bar. The pump device 16 is a compressor in this embodiment. Thereafter, a compression to approximately 60 bar takes place by means of a compression device 18 in a second pressure vessel 19 connected downstream of the compression device 18.

If compressed gas is utilized for driving the pump device 16, then the cold, which is generated with the expansion, can be used to cool the pump device 16. The second pressure vessel 19 is disposed in a cooling apparatus 20 having a temperature T which is so adjusted that the xenon, which is to be recovered, in the second pressure vessel changes over into a liquid phase. The temperature T is furthermore so selected that that impurity, which would next change over into the liquid phase at the temperature T, will just remain in the gas phase. Since the pressure P and the temperature T within the second pressure vessel 19 are coupled to each other via the gas equation, the temperature T must be made to track when a pressure change occurs in order to maintain the desired liquid aggregate state of the xenon.

A discharge device 22 having a discharge throttle 33 is connected to a gas-metering connection stub 21 of the second pressure vessel 19 in order to discharge individual residual gas constituents from the second pressure vessel 19 such as oxygen. A fill level sensor 23 is likewise connected to the connecting stub 21 and monitors so that no liquified xenon can flow off via the discharge device 22 and a pressure sensor 32 measures the pressure P within the second pressure vessel 19.

Residual gases are discharged from the second vessel 19 down to a pressure $P_{min}$ of 63 bar and, thereafter, the gases taken out of the first pressure vessel 17 are compressed to a pressure $P_{max}$ of 65 bar. In this way, the portion of liquid xenon in the second pressure vessel 19 is continuously increased. A third pressure vessel 24 is provided within the cooling apparatus 20 as an additional reservoir for liquid xenon. The pressure vessel 24 is connected via transport line 25 and a pump device 26 to the base 28 of the second pressure vessel 19. The pump device 26 transports liquid xenon from the second pressure vessel 19 into the third pressure vessel 24. When sufficient xenon has been pumped out of the second pressure vessel 19, the transport line 25 is shut off by a valve 29. A fill level detector 27 is provided at the fill connection 30 of the third pressure vessel. The fill level detector 27 is utilized to monitor that only liquid xenon is pumped into the third pressure vessel. A control apparatus 31 in the form of a microprocessor logic unit assumes all open-loop and closed-loop control tasks which occur.

The operation of the anesthesia arrangement shown in the drawing will now be described.

The expired respiratory gas containing xenon flows out of the anesthesia apparatus 1 and is first collected in the reservoir 5. The fill level within the reservoir 5 is monitored by the difference pressure sensor 7. If the measured difference pressure exceeds a preselected limit value, then the safety valve 4 is driven so that the expiration line 2 conducting the respiratory gas is connected to the anesthetic gas transport line 8. The safety valve 4 is connected between the anesthesia apparatus 1 and the reservoir 5. A switchover of this kind can, for example, be necessary when the pump device 16 is defective and no gas can be taken from the reservoir 5. The purification unit 9 is connected downstream of the reservoir 5 and removes suspended particles from the respiratory gas and eliminates vaporous contaminants with the active-charcoal filter. These contaminants are added to the respiratory gas because of the metabolism of the patient. Other vaporous constituents can be eliminated with the temperature device 11 by directly freezing the vaporous constituents out. The nitrogen portion, carbon dioxide portion and nitrous oxide portion in the respiratory gas are removed by means of the molecular sieve 12. After passing through the purification unit 9, the respiratory gas contains essentially only oxygen and xenon. After the respiratory gas is compressed by means of the pump device 16 to approximately 16 bar in the first pressure vessel 17, a further compression to approximately 60 bar is carried out in the second pressure vessel 19 with the compression unit 18.

The temperature T of the cooling arrangement 20 surrounding the second pressure vessel 19 is adjusted to approximately 10° C. so that xenon is condensed out and collected at the base 28 of the second pressure vessel 19.

The temperature T is so selected that only xenon is present in the liquid phase and all other gas constituents are present in gaseous form.

The pressure sensor 32 continuously registers the pressure P within the second pressure vessel 19. If a pressure $P_{max}$ of 65 bar is reached, then the compression unit 18 is switched off and the discharge device 22 is driven via the control apparatus 31 in such a manner that the gas flow from the compression unit 18 to the second pressure vessel 19 is interrupted and so that the gaseous constituents located in the second pressure vessel 19 above the xenon can escape via a discharge throttle 33 connected downstream of the discharge device 22.

When the pressure in the second pressure vessel 19 has reached the value $P_{min}$ of 63 bar, the discharge device 22 is again switched back into the initial position and the compression device 18 again compresses the gas in the second pressure vessel to the value $P_{max}$=65 bar. With this alternating action of "compression" and "discharge", the portion of liquid xenon slowly increases in the second pressure vessel 19 and liquid xenon can, as required, be transferred via pump line 25, the valve 29 and the pump device 26 into the third pressure vessel 24. Pure xenon can then again be taken from time third pressure vessel 24 for inhalation anesthesia.

It is understood that the foregoing description is that of the preferred embodiments of the invention and that various changes and modifications may be made thereto without departing from the spirit and scope of the invention as defined in the appended claims.

What is claimed is:

1. An anesthesia arrangement for ventilating a patient with a respiratory gas containing an anesthetic agent, the arrangement comprising:

an anesthesia apparatus having an expiration line for passing said respiratory gas from the patient;

a purification unit connected to said expiration line for removing contaminants and predetermined vaporous or gaseous components from said respiratory gas so as to leave a purified respiratory gas containing said anesthetic agent and any remaining vaporous or gaseous component or components;

a first pressure vessel;

pump means for pumping said respiratory gas through said purification unit and pumping said purified respiratory gas into said first pressure vessel;

a second pressure vessel connected to said first pressure vessel downstream thereof;

compressor means for moving said purified respiratory gas from said first pressure vessel and into said second pressure vessel;

cooling means for cooling said second pressure vessel;

control means for controlling said compressor means and said cooling means to operating parameters within said second pressure vessel which cause said anesthetic agent to assume a liquid phase in said second pressure vessel;

said anesthetic agent having a critical temperature;

said control means controlling said compressor means and said cooling means to set a pressure (P≅60 bar) and a temperature (T≅10° C.) within said second pressure vessel; and, said temperature (T≅10° C.) being less than said critical temperature.

2. The anesthesia arrangement of claim 1, wherein said remaining vaporous or gaseous components of said purified respiratory gas have respectively different critical temperatures less than said critical temperature of said anesthetic agent; and, said control means includes means for controlling said cooling means to set said temperature T to a value less than said critical value of said anesthetic agent.

3. The anesthesia arrangement of claim 1, said purification unit including a sorption filter and a temperature device for the vaporous or gaseous components.

4. The anesthesia arrangement of claim 1, wherein said anesthetic agent is xenon.

5. An anesthesia arrangement for ventilating a patient with a respiratory gas containing an anesthetic agent, the arrangement comprising:

an anesthesia apparatus having an expiration line for passing said respiratory gas from the patient;

a purification unit connected to said expiration line for removing contaminants and predetermined vaporous or gaseous components from said respiratory gas so as to leave a purified respiratory gas containing said anesthetic agent and any remaining vaporous or gaseous component or components;

a first pressure vessel;

pump means for pumping said respiratory gas through said purification unit and pumping said purified respiratory gas into said first pressure vessel;

a second pressure vessel connected to said first pressure vessel downstream thereof;

compressor means for moving said purified respiratory gas from said first pressure vessel and into said second pressure vessel;

cooling means for cooling said second pressure vessel;

control means for controlling said compressor means and said cooling means to operating parameters within said second pressure vessel which cause said anesthetic agent to assume a liquid phase in said second pressure vessel;

a third pressure vessel; and, a transport line connecting said second pressure vessel to said third pressure vessel for conveying said anesthetic agent in the liquid phase to said third pressure vessel.

6. The anesthesia arrangement of claim 5, further comprising ancillary pump means connected into said transport line for pumping the liquid anesthetic agent from said second pressure vessel to said third pressure vessel.

7. The anesthesia arrangement of claim 6, further comprising discharge means connected to said second pressure vessel for discharging the vaporous or gaseous components therein which are disposed in elevation above the liquified anesthetic agent.

* * * * *